United States Patent
Karremans et al.

(10) Patent No.: US 11,730,183 B2
(45) Date of Patent: Aug. 22, 2023

(54) MATERIAL FOR DE-DUSTING GRANULAR ENZYME PREPARATIONS

(71) Applicant: Mauri Technology B.V., Etten-Leur (NL)

(72) Inventors: Adrianus Rutgerus Antonius Karremans, Zevenbergschen Hoek (NL); Martinus Gerardus van Oort, Utrecht (NL)

(73) Assignee: Mauri Technology B.V., Etten-Leur (NL)

( * ) Notice: Subject to any disclaimer, the term of this patent is extended or adjusted under 35 U.S.C. 154(b) by 10 days.

(21) Appl. No.: 17/829,549

(22) Filed: Jun. 1, 2022

(65) Prior Publication Data
US 2022/0287351 A1 Sep. 15, 2022

Related U.S. Application Data

(62) Division of application No. 15/543,118, filed as application No. PCT/NL2015/050021 on Jan. 13, 2015, now Pat. No. 11,399,561.

(51) Int. Cl.
| | | |
|---|---|---|
| *A23P 10/47* | (2016.01) | |
| *A21D 8/04* | (2006.01) | |
| *A23L 29/00* | (2016.01) | |
| *A23L 29/212* | (2016.01) | |
| *A21D 2/16* | (2006.01) | |
| *A21D 2/18* | (2006.01) | |
| *A23D 9/00* | (2006.01) | |
| *A21D 2/00* | (2006.01) | |
| *C12N 9/98* | (2006.01) | |
| *A23P 10/40* | (2016.01) | |
| *A21D 10/00* | (2006.01) | |

(52) U.S. Cl.
CPC .............. *A23P 10/47* (2016.08); *A21D 2/00* (2013.01); *A21D 2/165* (2013.01); *A21D 2/186* (2013.01); *A21D 8/042* (2013.01); *A21D 10/005* (2013.01); *A23L 29/06* (2016.08); *A23L 29/212* (2016.08); *A23P 10/40* (2016.08); *C12N 9/98* (2013.01); *A23D 9/00* (2013.01)

(58) Field of Classification Search
CPC ........ A23P 10/47; A23L 29/06; A23L 29/212; A21D 2/165; A21D 2/186; A21D 8/042; A23D 9/00
See application file for complete search history.

(56) References Cited

U.S. PATENT DOCUMENTS

| | | |
|---|---|---|
| 3,987,207 A | 10/1976 | Spaeti et al. |
| 5,739,091 A | 4/1998 | Kiesser et al. |
| 6,063,822 A | 5/2000 | Suzuki |
| 6,403,549 B1 | 6/2002 | De Lima et al. |
| 2010/0068341 A1 | 3/2010 | Lohscheidt |
| 2012/0263825 A1 | 10/2012 | Diener et al. |

FOREIGN PATENT DOCUMENTS

| | | |
|---|---|---|
| EP | 0289069 A2 | 11/1988 |
| EP | 1541027 A1 | 6/2005 |
| EP | 2047752 A1 | 4/2009 |
| WO | 9501727 A1 | 1/1995 |
| WO | 199742839 A1 | 11/1997 |
| WO | 2012033399 A1 | 3/2012 |
| WO | 2013050286 A1 | 4/2013 |
| ZA | 9801675 A | 8/1999 |

OTHER PUBLICATIONS

National Sunflower Association, "Sunflower Oil fatty Acid Profiles" Oct. 2, 2010 https://web.archive.org/web/20201002083423/https:www.sunflowernsa.com/health/sunflower-oil-fatty-acid-profiles/ (2010).

*Primary Examiner* — Katherine D Leblanc
(74) *Attorney, Agent, or Firm* — Hoffmann & Baron, LLP

(57) ABSTRACT

The invention relates to a granular de-dusting material comprising
  30-60 wt. % cold-swelling potato starch,
  5-40 wt. % vegetable oil,
  5-35 wt. % flour,
  all weight percentages based on dry weight of the granular de-dusting material.
The invention further relates to a method for preparing a de-dusted enzyme product, comprising contacting a granular enzyme preparation, containing dust particles, with a granular dedusting material according to the invention, whereby the dust particles adhere to the granular de-dusting material, whereby the de-dusted enzyme product is obtained.
The invention further relates to a de-dusted enzyme product.

27 Claims, No Drawings

MATERIAL FOR DE-DUSTING GRANULAR ENZYME PREPARATIONS

CROSS-REFERENCE TO RELATED APPLICATIONS

This application is a Divisional Application of U.S. National Phase Application No. 15/543,118 filed Jul. 12, 2017, which claims priority from, International Patent Application Number PCT/NL2015/050021 filed 13 Jan. 2015, the contents of which are incorporated herein by reference.

The invention relates to a granular de-dusting material, to a method for preparing such material, to a method for de-dusting an enzyme preparation, to a granular enzyme product, to the use of a granular enzyme product as a bakery ingredient and to a method for preparing a baked product.

Enzymes are used for various food technology applications, e.g. in bakery application, brewery applications, in wine-making or in the preparation of dairy foods, but are also useful in processing (bio)molecules in general, e.g. for the hydrolysis of biomolecules (proteins, polysaccharides, triglycerides), in isomerisation processes.

In bakery applications, added enzymes are used—amongst others to improve dough processing, bread volume, or shelf-life (anti-staling). An example of a publication describing the use of enzyme mixtures to improve shelf-life is EP-A 1 541 027.

In particular in bakery applications, the enzymes are often used in a mixture with other conditioning agents, for example, with emulsifiers, salts, fats. The enzymes are usually employed as a powder, thereby facilitating a homogeneous distribution when mixed with other dough ingredients (such as flour) or added to a dough. In spite of the granular form, these enzyme products, typically contain dust particles (ultrafine particles, determinable with the Heubach test) which can easily be inhaled.

Similar to other protein allergens, enzymes may cause respiratory allergy or occupational asthma when inhaled. Allergy symptoms are similar to hay fever and may include persistent sneezing, a runny nose, watery eyes, breathing difficulties and coughing.

During normal handling, such as removal from packaging, pouring a granular enzyme product into flour mixtures or during addition of an enzyme preparation to the dough, enzyme dust may be formed and thus, there is a substantial risk that dust is inhaled and that enzymes in the dust penetrates into the lungs of people exposed to the dust. Therefore, special precautions are needed to safeguard the work force handling the enzyme products from such exposure.

An allergy against (dust of) enzymes will typically develop according to the following route:

Exposure: Inhalation of airborne allergens (dust or aerosols). The level of dust exposure as well as the composition of the dust has a clear effect on the incidence of occupational asthma.

Sensitization: Some people are sensitized when exposed to enzymes. Their immune system is activated and these people will have a positive skin or blood test. At this stage they still don't have any symptoms.

Allergy. Some sensitized people develop an allergy when they are repeatedly exposed to the same enzyme . In this case they will have a positive skin or blood test and they will suffer from allergy related symptoms.

The Health Council of the Netherlands has issued a report regarding the recommended occupational exposure limit of fungal Alpha-amylase (derived from the fungus *Aspergillus oryzae*). This report mentions a minimal exposure level of 0.9 μg/m$^3$, The Hague: Health Council of the Netherlands, 2014; publication no. 2014/25. ISBN: 978-94-6281-017-4).

One way to address the problem of dusting, is to use liquid enzyme preparations. However, as discussed in WO 1997/042839A1, liquid preparations have drawbacks, such as lack of enzyme stability and enzyme-inactivation and on top of that, liquid preparations may form aerosols during processing which can also be inhaled with similar consequences as dust inhalation.

Accordingly, WO 1997/042839A1 describes an enzyme granulate with low dust content, which granulate is obtainable by initially producing a moist granulate comprising an enzyme and an organic flour, which flour has been obtained by grinding a flour source treated with dry superheated steam; and wherein the enzyme, flour and optionally granulation auxiliaries are mixed with water to establish a moisture content in the moist granulate of 20 to 50 wt. % in a rapid mixer by intensive mixing, with at least occasional use of a knife head to form a tack-free, moist granulate with particles in the desired particle size range and drying the moist granulate. In particular, the granulate is characterized by the fact that it consists of a granulate core with the composition 0.08 to 22 wt. % (dry substance) enzyme, 55 to 96.92 wt. % (dry substance) of a flour type with a degree of grinding of 30 to 100%, wherein the flour type was obtained by the grinding of a flour source treated with dry superheated steam; perhaps up to a total of 18.5 wt. % enzyme- and nutrition-physiologically compatible granulating auxiliaries (calculated as anhydrous substance); 3 to 12 wt. % moisture, wherein the sum of the preceding components of the granulate core is 100 wt. %.

A drawback of the methodology of WO 1997/042839A1 is the need to add water and the need to apply a drying step. Further a mixer with a knife head is needed to mix the enzyme, containing the dust, the water and the flour. These aspects add to complexity of the methodology and, in particular the use of water and/or the drying step may also affect the properties of the enzyme. Further, a relatively large amount of flour is needed.

It is an object of the present invention to provide an alternative to known ways of providing granular enzyme products that have a low dust content.

In particular it is an object to overcome one or more drawbacks of the technology described in the prior art.

One or more further objects are apparent from the description herein below.

It has now been found possible to provide a specific de-dusting material, that can be used to de-dust a granular enzyme preparation, by mixing the de-dusting agent with the enzyme preparation.

Accordingly, the invention relates to a granular material (suitable for de-dusting a granular product, such as a granular enzyme preparation) comprising
30-60 wt. % cold-swelling potato starch,
5-40 wt. % vegetable oil, and
5-35 wt. % flour,
all weight percentages based on dry weight of said granular material.

The invention further relates to a method for preparing the granular material according to the invention, the method comprising blending the potato starch, the vegetable oil and the flour thereby obtaining the granular material.

It has surprisingly be found that by the use of specifically the cold-swelling potato starch, the vegetable oil and the flour in an amount within the specified ranges, a granular material is obtainable with satisfactory free flowing capability to allow mixing with a granular enzyme material to be de-dusted, yet also having the capacity to effectively reduce the dust content of a granular material, such as a granular enzyme preparation, as determinable by the Heubach method. This methodology is practiced in accordance with the DIN 55 992 standard (*American Industry Hygiene Association Journal* (1990) April; 51(4):210-6.)

Accordingly, the invention in particular further relates to the use of a granular material according to the invention as a de-dusting agent for a granular material, in particular a granular enzyme preparation.

Accordingly, the invention further relates to a method for preparing a de-dusted enzyme product, comprising contacting a granular enzyme preparation, containing dust particles, with a granular de-dusting material according to the invention, whereby the dust particles adhere to the granular de-dusting material, whereby the de-dusted enzyme product is obtained.

In particular, it has surprisingly been found that a method of the invention is suitable to provide a granular free-flowing enzyme product which is essentially dust-free. Further, the invention allows the preparation of such product without the need for adding water and without the need for a drying step. Further, the preparation can be carried out in simple mixing equipment, e.g. a mixing drum, without special means to ensure effective contacting the enzyme preparation and the de-dusting agent. The de-dusting material generally consists of ingredients that are generally regarded as safe for animal or human consumption (GRAS-ingredients). Accordingly, there is no need to remove the de-dusting material from the de-dusted enzyme product. Thus, the de-dusted product can be further used as such, optionally after combining the product with one or more further (GRAS) ingredients.

Accordingly, the invention further relates to a granular enzyme product composed of
one or more enzymes (other than the enzymes which may be naturally present in the ingredients for the de-dusting material; in particular potato starch and flour may comprise enzymes),
granular material according to the invention,
and optionally one or more further ingredients.

The enzyme product has been found particular useful in bakery applications. Accordingly, the invention further relates to the use of a granular enzyme product according to the invention as a bakery ingredient.

In particular, the enzyme product may be added to dough or be mixed with other ingredients for preparing a dough. Thus, the invention further relates to a method for preparing a baked product comprising preparing a dough using a granular enzyme product according to the invention, thereby obtaining a dough comprising the enzyme or enzymes of the granular enzyme product, and baking the dough comprising the enzyme or enzymes of the granular enzyme product.

The invention further relates to a baked product obtained by a method of the invention. Preferably the baked product is selected from the group of bread, rolls, buns, cookies, pastry and (flour) tortillas.

Unless defined otherwise, all technical and scientific terms used herein have the same meaning as commonly understood by one of ordinary skill in the art.

The term "or" as used herein means "and/or" unless specified otherwise.

The term "a" or "an" as used herein means "at least one" unless specified otherwise.

The term "essential(ly)" is generally used herein to indicate that it has the general character or function of that which is specified. When referring to a quantifiable feature, this term is in particular used to indicate that it is more than 90%, more in particular more than 95%, even more in particular more than 98% of the maximum that feature. The term 'essentially free' is generally used herein to indicate that a substance is not present (below the detection limit achievable with analytical technology as available on the effective filing date) or present in such a low amount that it does not significantly affect the property of the product that is essentially free of said substance or that it is present in such a low amount (trace) that it does not need to be labelled on the packaged product that is essentially free of the substance. In practice, in quantitative terms, a product is usually considered essentially free of a substance, if the content of the substance is 0-0.1 wt. %, in particular 0-0.01 wt. %, more in particular 0-0.005 wt. %, based on total weight of the product in which it is present.

The term "about" in relation to a value generally includes a range around that value as will be understood by the skilled person. In particular, the range is from at least 10% below to at least 10% above the value, more specifically from 5% below to 5% above the value.

When referring to a "noun" (e.g. a compound, an additive etc.) in singular, the plural is meant to be included, unless specified otherwise.

As used herein "dust" means (dust) particles as determined by the Heubach test (Authors: ESA STAT Dust Working Group, Version: 1.0. Date: 23 Mar. 2011© ESA European Seed Association aisbl) and American Industry Hygiene Association Journal (1990) April; 51(4):210-6, of which the contents, in particular the contents describing the test, are enclosed herein by reference.

As used herein the particle size or average particle size is the particle size as determinable with Retsch sieve according to DIN 4188.

For the purpose of clarity and a concise description features are described herein as part of the same or separate embodiments, however, it will be appreciated that the scope of the invention may include embodiments having combinations of all or some of the features described.

The granular material of the invention without having been mixed with the material to be de-dusted is referred to herein below as the granular de-dusting material.

The cold-swelling potato starch, vegetable oil plus flour usually form 90-100 wt. % based on dry weight, of the granular de-dusting material. Preferably, the total content of cold-swelling potato starch, vegetable oil plus flour is 95-100 wt. %, in particular 99-100 wt. %, based on total dry weight. The water-content of the granular de-dusting material is generally less than 10 wt. %, in particular less than 6 wt. %. This is advantageous amongst others for good flowing properties of the granular material.

The granular de-dusting material usually essentially consists of substances of vegetable origin. In particular, it is essentially free of substances of animal origin. Usually the de-dusting material is essentially free of genetically modified substances or substances from genetically modified organisms, although in principle such substances can be used to prepare the granular de-dusting material. In an advantageous embodiment, the granular de-dusting material is essentially free of Crustaceans and products thereof, Eggs and products thereof, Fish and products thereof, Peanuts and products thereof, Soybeans and products thereof, Milk and products thereof (incl. Lactose), Nuts i.e. almonds *Amygdalus communis L.*), hazelnuts (*Corylus avellana*), walnuts (*Juglans regia*), cashews (*Anacardium occidentale*), pecan nuts (*Carya illinoiesis*), Brazil nuts (*Bertholletia excelsa*), pistachio nuts (*Pistacia vera*), macadamia nuts and Queensland nuts (*Macadamia ternifolia*), and products thereof, Celery and products thereof, Mustard and products thereof, Sesame Seeds and products thereof, Lupin and products thereof, and Molluscs and products thereof. These substances are preferably absent because of their potential allergenic activity.

The granular de-dusting material usually has a particle size wherein at least 95% of the weight of the material has a size <3.0 mm, preferably at least 95% <2.5 mm, in particular of at least 95% <2.0 mm. This is achieved by sieving all raw materials prior to blending. The average particle size (used for preparation) of the granular de-dusting material usually is in the range of 0.15-0.30 mm, preferably 0.18-0.25 mm, in particular about 0.22 mm.

The granular de-dusting material comprises cold-swelling potato starch. The term 'cold-swelling' is generally known in the art, meaning that the potato starch thickens when mixed with cold water, such as water having a temperature of about 20° C. Cold-swelling potato starch is distinct from potato starch as is found in nature. It is generally obtained by physical modification of potato starch as is found in nature. It is generally known how to provide cold-swelling potato starch. In particular this is achieved by pre-gelatinising starch. Cold-swelling (pre-gelatinised) potato starch is readily commercially available.

In particular, good results have been achieved with granular de-dusting material made from or comprising cold-swelling potato starch with a specific bulk density of about 50-150 g/100 ml.

The potato starch (used for preparation) of the granular de-dusting material usually has a particle size wherein at least 95% of the weight is <2.0 mm, preferably at least 95% <1.5 mm. In particular, good results have been achieved with potato starch having a particle size of at least 95% <1.0 mm. The average particle size of the potato starch usually is in the range of 5-100 µm. Without being bound by theory, it is thought that potato starch having cold-swelling properties, a relatively low particle size and/or a relatively low bulk density is advantageous to adsorb vegetable oil onto/into the potato starch particles in such a way that the granular de-dusting material on the one hand has good de-dusting properties (due to good adherence of dust particles to the de-dusting material) and on the other hand has satisfactory flowability, which is also desirable for efficient de-dusting action and for further handling of the de-dusted product.

In a preferred embodiment, the potato starch is obtainable by a drum drying, extrusion cooking, spray drying, annealing, heat-moisture treatment or high hydrostatic pressure treatment.

The potato starch usually comprises amylose and amylopectin; typically it comprises 15 to 25 wt. % amylose and 75 to 85 wt. % amylopectin, based on dry weight, in particular it contains amylose and amylopectin in a weight to weight ratio of about 20:80. The starch usually is not chemically modified.

The content of the potato starch in the granular de-dusting material preferably is 50 wt. % or less, more preferably 45 wt. % or less, in particular about 43 wt. % or less, more in particular about 40 wt. % or less. In a specific embodiment, the content of the potato starch is at least 33 wt. %. A relatively high potato starch content is favourable for improved de-dusting efficiency. Further, obtaining a de-dusting material with a more homogeneous distribution of potato starch, flour and vegetable oil is facilitated with a relatively high potato starch content. Lowering the starch content is advantageous for improved free-flowing properties.

The term "oil" is used herein for any fat that is essentially fluid at 25° C. It should be noted though that in an oil that is a mixture of different fats, in principle a minor amount of solid fat (e.g. 10 wt. % or less) may be present that is solid at 25° C., as long as the mixture of all fats is essentially fluid at 25° C.

The vegetable oil content of the granular de-dusting material preferably is at least 15 wt. %, more preferably at least 25 wt. %, in particular at least 30 wt. %, based on dry weight. Preferably, the vegetable oil content is about 35 wt. % or less. In a specific embodiment the vegetable oil content is 33 wt. % or less, more specifically 31 wt. % or less. In general, a higher vegetable oil content increases the de-dusting efficiency. A too high vegetable oil content may have an adverse effect on flowability of the granular de-dusting material or enzyme product obtained after de-dusting.

The vegetable oil usually is an oil at least substantially consisting of triglycerides. The oil preferably contains both one or more saturated fatty acids and one or more unsaturated fatty acids. The term 'fatty acid' is used herein in the commonly used sense in food technology and thus includes not only free fatty acid but also fatty acid residues in fatty acids esters, such as in triglycerides. Generally, essentially all the fatty acid will be present as part of a glyceride, in particular a triglyceride.

Good results have been achieved with a granular de-dusting material wherein the vegetable oil comprises at least one saturated fatty acid, at least one mono-unsaturated fatty acid and at least one poly-unsaturated fatty acid. The fatty acid content is preferably for 80-100% composed of fatty acids having 12-24 carbon atoms.

Preferably, the saturated fatty acid content is less than 20 wt. % more preferably 15 wt. % or less, in particular 5-10 wt. %, based on total fatty acids. Preferred saturated fatty acids are palmitic acid and stearic acid. Preferably, 50-100%, in particular 90-100% of the saturated fatty acid content is provided by palmitic acid and/or stearic acid.

The monounsaturated fatty acid content preferably is 70 wt. % or more, more preferably at least 75 wt. %, more preferably 80-90 wt. %, based on total fatty acids. Preferably oleic acid provides 50-100%, in particular 90-100% of the mono-unsaturated fatty acid content.

The poly-unsaturated fat content preferably is at least 1 wt. %, more preferably at least 3 wt. %, in particular at least 5 wt. %. The content is usually less than 20 wt. %, in particular less than 15 wt. %, preferably 10 wt. % or less, based on total fatty acids. Higher levels of polyunsaturated fatty acids will lead to undesired smell upon storage and upon use in bakery applications in combinations with lipases. Linoleic acid is a preferred polyunsaturated fatty acid. Preferably, 50-100%, in particular 90-100% of the polyunsaturated fatty acid content is provided by linoleic acid.

In a specific embodiment, the vegetable oil comprises:
  palmitic acid and stearic acid, in a total concentration of 6-10 wt. %, based on total fatty acids, e.g. in a weight to weight ratio of about 0.8:1 to 1.2:1;
  80-88 wt. % oleic acid, based on total fatty acids;
  6-10 wt. % linoleic acid, based on total fatty acids.

In particular suitable is granular de-dusting material wherein the vegetable oil comprises one or more oils or fractions of oils selected from the group of soybean oil, canola oil, sunflower oil, safflower oil, peanut oil, cottonseed oil, coconut oil, palm oil, rice bran oil, respectively fractions of said oils.

Particularly good results have been achieved with a granular de-dusting material comprising sunflower oil, preferably at least 50 wt. %, more preferably at least 75 wt. %, in particular at least 80 wt. % sunflower oil, based on total oil. The sunflower oil content is up to 100%, based on total oil. If oil from another source is present, the sunflower oil content usually is 99 wt. % or less, in particular 95 wt. % or less.

Preferably, the vegetable oil has a high oleic acid content, such as a oleic acid content of 69 wt. % or more, based on total fatty acids. Preferably it comprises at least about 82 wt. % oleic acid. High oleic acid sunflower oil, i.e. sunflower oil comprising at least about 82 wt. % oleic acid, based on total fatty acids, is a particularly suitable vegetable oil.

The vegetable oil (used in the preparation) of a granular de-dusting material of the invention preferably has been subjected to a de-watering treatment (refined), such that it is essentially water-free.

The flour content of the granular de-dusting material preferably is at least 15 wt. %, more preferably at least 20 wt. %, in particular at least 25 wt. %, more in particular at least 30 wt. %, based on dry weight. In a specific embodiment the flour content is 33 wt. % or less, more specifically 31 wt. % or less. The flour in particular contributes to the free-flowing properties of the de-dusting material, and contributes to satisfactory flowing properties of the de-dusting material also in the presence of the vegetable oil (which one would expect to be detrimental to flowability). For good flowing properties in combination with satisfactory de-dusting effectivity it is preferred that the ratio of the vegetable oil to the flour is in the range 1:2 to 2:1, in particular in the range of 1:1.5 to 1.5:1, more in particular about 1:1.

Usually the flour is selected from the group of cereal flours and *Fabaceae* flours.

Examples of *Fabaceae* flours are flours from *pisum* (peas), *cajanus* (pigeon pea), *cicer* (chick-pea), *lens* (lentils); *phaseolus* (beans), *vigna* (cowpeas), dolichos (hyacinth beans), *canavalia* (sword bean), *vicia* (sweet peas) and lima beans. Peanuts or soybean may also provide suitable flour, but may be allergenic to many people.

Preferably, the flour of the de-dusting material comprises 50-100 wt. %, in particular 90-100 wt. %, more in particular 99-100 wt. % cereal flour. Examples of cereal flours are flours from barley, corn, millet (e.g. sorghum), oats, rice, rye and wheat. In particular good results have been achieved with wheat flour. Thus, preferably 50-100 wt. %, in particular 90-100 wt. % of the flour of the granular de-dusting material is wheat flour.

Preferably, the flour has a low moisture content, in particular a moisture content of less than 6 wt. %. Such flour is commercially available or can be obtained using a generally known drying technique. Good results have been achieved with a granular de-dusting material, wherein at least part of the flour is a flour that has been heat-treated, e.g. with superheated steam. Suitable heat-treated flour is commercially available, e.g. from Fazer, Finland or can be made with methodology known in the art per se, see e.g. WO 1997/042839A1. Preferably, 50-100% is heat-treated flour, in particular 75-99% is heat-treated flour, more in particular 90-98% is heat-treated flour.

The granular de-dusting material of the invention can be obtained by blending the potato starch, the vegetable oil and the flour, thereby obtaining the granular material. The ingredients are usually blended in dry form, the water-content of the ingredients in general being less than 10 wt. %, in particular less than 6 wt. %. In particular the vegetable oil, preferably is de-watered such that it is essentially free of water (having a maximum water content of 0.1%).

The preparation can be carried out in conventional mixing equipment, e.g. in a conical blender, to obtain a granular material with satisfactory free flowing capability and de-dusting capability. The mixing time needed to obtain the product can routinely be determined. It usually is in the range of 1-90 min, in particular in the range of 5-60 min, more in particular in the range of 10-30 min.

The temperature can be chosen within wide ranges, at a temperature known to be acceptable for processing the ingredients, typically in the range of 0-75° C., in particular in the range of 10-40° C., more in particular 20-30° C. The process can usually be carried out at ambient temperature or higher, albeit that the temperature preferably is at or above the melting temperature or melting range of the vegetable oil.

As the method is usually carried out without adding water, the method usually is free of a drying step.

A method according to the invention for de-dusting a dusty granular product, in particular a granular enzyme preparation, comprises contacting a granular enzyme preparation, containing dust particles, with a granular de-dusting material according to the invention. Hereby, the dust particles adhere to the granular de-dusting material. Thereby the de-dusted enzyme product is obtained. Since the dust particles generally remain in the product, there is no (significant) loss of activity in the enzyme preparation. The contacting can be carried out in generally used equipment, such as a mixing drum or a fluidized bed apparatus.

The contacting is usually carried out at ambient temperature or higher, preferably at a temperature of 20° C. or more. The upper limit is determined in particular by the maximum temperature at which can be contacted without substantially deteriorating the granular de-dusting material or the material to be de-dusted. Thus, the temperature is below a temperature at which an enzyme preparation to be de-dusted would suffer from inactivation. In general, the temperature will be below 70° C., in particular 50° C. or less, more in particular 35° C. or less. The contact time needed to obtain the de-dusted product can routinely be determined. The contacting time usually is in the range of 1-90 min, in particular in the range of 5-60 min, more in particular in the range of 10-30 min.

The granular de-dusting material and the granular enzyme preparation to be de-dusted are usually contacted during the de-dusting method in a weight to weight ratio of at least 0.5:99.5, preferably in a ratio of at least 1.0:99.0, more preferably in a ratio of at least 2.5:97.5. The upper limit is not particularly critical, and may be relatively high in particular if the de-dusted product does not need to have a high enzyme content. Usually satisfactory de-dusting is accomplished at a weight to weight ratio granular de-dusting material to granular enzyme preparation of less than 50:50. Preferably, said ratio is 30:70 or less, more preferably 15:80 or less, in particular 5:95 or less, in particular 3.5:96.5 or less. A relatively low ratio is preferred in that thus an enzyme product with a high enzyme content is obtained. Moreover, at least in some embodiments this is advantageous for the flowing properties.

The enzyme preparation usually comprises one or more enzymes useful in a process for the preparation of a food, in particular one or more enzymes for use in the preparation of a bakery product, such as a bread, pastry, or cookie or in the preparation of a flour tortilla.

In principle any type of granular enzyme preparation can be de-dusted with a method of the invention. The enzyme preparation usually at least substantially consists of one or more enzymes.

Generally, the enzyme preparation comprises one or more enzymes selected from the group of amylases, in particular fungal amylases, bacterial amylases, maltogenic amylases; xylanases; lipases; phospholipases; galactolipases; proteases; peptidases; oxidases; transglutaminases; laccases and amyloglucosidases.

The de-dusting method of the invention in particular allows a dust reduction of more than 50%, more in particular of more than 90%. The de-dusted enzyme product (obtainable with a method) according to the invention usually has a dust content as determinable by Heubach dust analysis method, of less than 500 ppm, preferably of less than 100 ppm, and most preferably less than 50 ppm. Preferably, the de-dusted enzyme product is essentially free of dust.

The de-dusted enzyme product usually is a dry product, the water-content in the granular material generally being less than 10 wt. %, in particular less than 6 wt. %.

The granular enzyme product of the invention may essentially consist of a blend of the granular de-dusting product and the granular enzyme preparation. If desired, one or more further ingredients may be added prior to use. E.g. a diluent, carrier material may be blended with the de-dusted product. Examples thereof are conventionally used materials such as a flour, dextrin, maltodextrin, starch or salt. The flour may be the same or different from the flour of the de-dusting material. In particular, it may be a starch flour of a root or tuber (e.g. potato or cassava), a *Fabaceae* flour (e.g. of a source as mentioned above) or a cereal flour (e.g. of a source mentioned above) or a mixture thereof. The flour may have been subjected to a prior heat treatment as described above or not.

Preferably, the granular de-dusted enzyme product has an enzyme content of 5-99.5 wt. %, a content of the granular material of the invention, of 0.5-30 wt. % and a content of the one or more further ingredients of 0-65 wt. %, all based on dry weight of the product.

The enzyme content preferably is 10-98 wt. %, more preferably 30-97 wt. %, in particular 50-95 wt. %, in particular 70-95 wt. %, based on dry weight of the product.

The content of the (substances originating from) the granular de-dusting material preferably is 1-5 wt. %, in particular 1-3 wt. %, based on dry weight of the product.

The one or more further ingredients, if present, usually are present in an amount of at least 1 wt. %, in particular of 5-50 wt. %, more in particular 10-30 wt. %.

The particle size of the granular enzyme product generally depends on the particle size of the starting materials from which the product has been made; in an embodiment of the invention >95 wt. % of the weight of the granular enzyme product has a particle size in the range of 0.01-1 mm, in particular in the range of 0.05-0.5 mm and more in particular in the range of 0.005-0.2 mm.

In particular, if the de-dusting enzyme is intended for use in a bakery application, the product usually comprises at least one enzyme selected from the group of fungal amylases, bacterial amylases, maltogenic amylases, xylanases, lipases, phospholipases, galactolipases, proteases, peptidases, oxidases, transglutaminases, laccases and amyloglucosidases. These enzymes can be employed for a reason known per se, e.g. improved dough handling, increased softness of the bread, improved shelf-life, increased loaf volume, e.g. as described in WO 2012/033399 for flour tortillas or in EP-A 1 541 027 or EP-A 2 047 752 for bread.

The contents of these publications are incorporated by reference, in particular with respect to information of the enzymes therein and their use in the preparation of a baked product.

The invention will now be illustrated by the following examples.

EXAMPLE 1

Formulation example:
Cold-swelling potato starch: about 43 wt. %
Cereal flour (wheat, heat treated): about 22 wt. %
Vegetable oil: about 35 wt. %
of which: 6-10 wt. % in total of palmitic acid and/or stearic acid, 80-88 wt. % oleic acid and 6-10 wt. % polyunsaturated fatty acid (all based on total fatty acids)
Moisture content: less than 6 wt. % (from ingredients, no added water)
The de-dusting material was obtained by blending the ingredients at room temperature.

EXAMPLE 2

43 wt. % cold swelling potato starch (moisture content <6 wt. %), 35 wt. % high oleic acid sunflower oil (refined, essentially free of water) and 22 wt. % heat-treated wheat flour (moisture content <6 wt. %)) were blended at room temperature and granulated.

The resultant granular de-dusting material was blended at room temperature with either a fungal amylase, with a bacterial amylase or a fungal lipase (at a wt. to wt. ratio of 3:97). Dust content was determined for the enzymes without the de-dusting material and after blending with the de-dusting materials. The Heubach test and a perception test by experienced operators were used. The results are shown in the following table.

| Example | Product | Dustiness as perceived by process operators experienced in working with enzymes | Dust (mg/kg) Heubach test |
| --- | --- | --- | --- |
| Ref. 2A | Fungal Amylase | Extremely dusty | 1970 |
| Ex. 2A | Fungal amylase with 3% de-dusting material according to the invention | Not dusty | 0 |
| Ref. 2B | Bacterial Amylase | Quite dusty | 1060 |
| Ex. 2B | Bacterial Amylase 1 with 4.8% de-dusting material according to the invention | Not dusty | 0 |
| Ref 2C | Fungal Lipase | Quite dusty | 1274 |
| Ex. 2B | Fungal Lipase with 3% de-dusting material according to the invention | Not dusty | 58 |

EXAMPLE 3

43 wt. % cold swelling potato starch (moisture content <6 wt. %), 35 wt. % high oleic acid sunflower oil (refined, essentially free of water) and 22 wt. % heat-treated wheat flour (moisture content <6 wt. %)) were blended at room temperature and granulated to form a granular de-dusting material.

Another granular de-dusting material was made in the same manner with the same ingredients, except that palm oil was used instead of the high oleic oil.

Another granular de-dusting material was made in the same manner with the same ingredients, except that regular sunflower oil was used instead of the high oleic oil.

The flowing properties of all three de-dusting materials were compared and it was found that the flowing properties of the material comprising high oleic sunflower oil were much better, thereby facilitating further handling and use in de-dusting applications. The flowing properties of the de-dusting material containing regular sunflower oil and of the material containing the palm oil were comparable

EXAMPLE 4

43 wt. % cold swelling potato starch (moisture content <6 wt. %), 35 wt. % high oleic sunflower oil (refined, essentially free of water) and 22 wt. % heat-treated wheat flour (moisture content <6 wt. %)) were blended at room temperature and granulated to form a granular de-dusting material.

Another granular de-dusting material was made in the same manner with the same ingredients, except that regular (not heat treated) wheat flour was used instead of the heat treated wheat flour.

It was found that a more homogeneous blend was obtained with the heat-treated flour and that the flowing properties of the de-dusting material comprising the heat-treated flour were much better, thereby facilitating further handling and use in de-dusting applications.

Further, a material was made of 43 wt. % cold swelling potato starch (moisture content <6 wt. %), 35 wt. % high oleic sunflower oil (refined, essentially free of water)but with 22 wt. % heat-treated soy flour (moisture content <6 wt. %)). The flowing properties were much lower than for the material made with heat-treated wheat flower, and also significantly lower than for the de-dusting material made with wheat-flour that had not been subjected to heat treatment.

The invention claimed is:

1. Method for preparing a de-dusted enzyme product, comprising contacting a granular enzyme preparation, containing dust particles, with a granular dedusting material, whereby the dust particles adhere to the granular de-dusting material, whereby the de-dusted enzyme product is obtained, wherein said de-dusting material is a granular de-dusting material comprising a mixture of
   30-60 wt. % cold-swelling potato starch,
   5-40 wt. % vegetable oil,
   5-35 wt. % flour,
   all weight percentages based on dry weight of the granular de-dusting material.

2. Method according to claim 1, wherein the granular de-dusting material and the granular enzyme preparation are contacted in a weight to weight ratio granular de- dusting material to granular enzyme preparation of 0.5:99.5 to 5:95.

3. Method according to claim 2, wherein the weight to weight is in the range of 1:99 to 15:85.

4. Method according to claim 3, wherein the weight to weight ratio is in the range of 2.5:97.5 to 3.5:96.5.

5. Method according to claim 1, wherein the enzyme preparation comprises one or more enzymes selected from the group of fungal amylases, bacterial amylases, maltogenic amylases, xylanases, lipases, phospholipases, galactolipases, proteases, peptidases, oxidases, transglutaminases, laccases and amyloglucosidases.

6. Method according to claim 1, wherein a de-dusted enzyme product is obtained that is essentially free of dust using the Heubach dust analysis method.

7. Granular de-dedusted enzyme product at least composed of one or more enzymes, having an enzyme content of 5-99.5 wt. %, a content of the granular material of 0.5-30 wt. % and a content of 0-65 wt. % of the one or more further ingredients, based on dry weight of the product, said granular material comprising a mixture of
   30-60 wt. % cold-swelling potato starch,
   5-40 wt.% vegetable oil,
   5-35 wt. % flour,
   all weight percentages based on dry weight of the granular de-dusting material.

8. A granular de-dusted enzyme product according to claim 7, having an enzyme content of 10-95 wt. % and a content of the granular material of 1-5 wt. %, in based on dry weight of the product.

9. A granular de-dusted enzyme product according to claim 8, comprising at least one enzyme selected from the group of fungal amylases, bacterial amylases, maltogenic amylases, xylanases, lipases, phospholipases, galactolipases, proteases, peptidases, oxidases, transglutaminases, laccases and amyloglucosidases.

10. Method for preparing a baked product comprising preparing a dough using a granular enzyme product according to claim 7, and baking the dough comprising the enzyme or enzymes of the granular enzyme product.

11. Method according to claim 1, wherein the granular de-dusting material comprises
   30-45 wt. % cold-swelling potato starch,
   30-35 wt. % vegetable oil,
   20-30 wt. % flour.

12. Method according to claim 1, wherein the granular de-dusting material essentially consists of vegetable ingredients.

13. Method according to claim 1, wherein said cold-swelling potato starch is pre-gelatinised.

14. Method according to claim 1, wherein said vegetable oil comprises at least one oil or at least one fraction of an oil selected from the group of soybean oil, canola oil, sunflower oil, safflower oil, peanut oil, cottonseed oil, coconut oil, palm oil, and rice bran oil.

15. Method according to claim 14, wherein said vegetable oil comprises sunflower oil.

16. Method according to claim 14, wherein said vegetable oil is dewatered oil.

17. Method according to claim 14, wherein said vegetable oil comprises high oleic acid sunflower oil.

18. Method according to claim 1, wherein said vegetable oil comprises at least one saturated fatty acid, at least one mono-unsaturated fatty acid and at least one poly-unsaturated fatty acid.

19. Method according to claim 18, wherein said vegetable oil has a saturated fatty acid content of 5-10 wt. %, a monounsaturated fatty acid content of 80-90 wt. %, and a poly-unsaturated fat content of 5-10 wt. %, based on total fatty acids.

20. Method according to claim 1, wherein the flour is cereal flour or Fabaceae flour.

21. Method according to claim 20, wherein the flour comprises cereal flour.

22. Method according to claim 20, wherein the flour comprises wheat flour.

23. Method according to claim 20, wherein the flour comprises granulated, heat-treated flour.

24. Method according to claim 1, wherein the material is free-flowing.

25. The method according to claim 21, the flour comprises 50-100 wt. % cereal flour, based on total flour.

26. The method according to claim 22, wherein the flour comprises 50-100wt. % wheat flour, based on total flour.

27. The method according to claim 15, wherein said vegetable oil comprises 50-100% sunflower oil.

* * * * *